United States Patent [19]
Kapsner et al.

[11] Patent Number: 6,063,368
[45] Date of Patent: May 16, 2000

[54] FOAMING HAIR CARE PRODUCT

[75] Inventors: Timothy Roland Kapsner, Minneapolis; Peter Matravers, Plymouth, both of Minn.

[73] Assignee: AVEDA Corporation, Blaine, Minn.

[21] Appl. No.: 09/126,460

[22] Filed: Jul. 30, 1998

[51] Int. Cl.[7] .............................. A61K 7/06; A61K 7/075
[52] U.S. Cl. ................. 424/70.1; 424/70.11; 424/70.28; 424/70.13; 424/70.16; 424/43; 424/47; 424/DIG. 2
[58] Field of Search ................................ 424/70.1, 70.11, 424/70.28, DIG. 1, DIG. 2, 70.13, 70.16, 43, 47; 514/881, 880, 945

[56] References Cited

U.S. PATENT DOCUMENTS

| 3,472,840 | 10/1969 | Stone et al. . |
| 4,165,367 | 8/1979 | Chakrabarti . |
| 4,744,978 | 5/1988 | Homan et al. . |
| 4,865,838 | 9/1989 | Gross et al. . |
| 5,603,919 | 2/1997 | Liu et al. . |
| 5,641,479 | 6/1997 | Linares et al. . |

FOREIGN PATENT DOCUMENTS

| 9313829A | 7/1993 | European Pat. Off. . |
| 97/13585 | 4/1997 | WIPO . |

*Primary Examiner*—Thurman K. Page
*Assistant Examiner*—Amy E Pulliam
*Attorney, Agent, or Firm*—Karen A. Lowney, Esq.

[57] ABSTRACT

The present invention relates to cosmetic compositions for topical application to the hair comprising effective amounts of effective amounts of a foaming agent, a water soluble acrylate or methacrylate polymer or copolymer, and a water soluble quaternized cellulose derivative. The compositions, when dispensed through a non-aerosol pump foaming apparatus, results in a foaming lightweight mousse-like product which excellent hold and conditioning to the hair.

20 Claims, No Drawings

FOAMING HAIR CARE PRODUCT

FIELD OF THE INVENTION

The present invention relates to hair-care compositions. More specifically, the invention relates to foaming hair styling and conditioning compositions.

BACKGROUND OF THE INVENTION

In recent years, the forms in which hair care products are available has expanded tremendously. In large part, this is due to continuous consumer demand for new products which perform not just one, but several benefits to the hair simultaneously, while also being pleasant to use. Providing such products can be a challenge to the industry, as when additional functions are added to a product, there is the increased potential for the interaction of the various components to interfere with each other's functions, thereby possibly affecting the performance of the product as a whole.

Among the characteristics most frequently desired by consumers in a hair care product are the ability to hold or manage the hair, while also providing conditioning to the hair. It is also preferred that the product be easy and pleasant to apply. There are of course a large number of different hair styling compounds available which alone will provide adequate hold to the hair upon application; these are most commonly cationic polymers. However, the addition of a conditioning agent, or in fact, any components other than the aqueous base, can reduce or plasticize the hold, thereby deleteriously affecting a main function of the product. Moreover, many conditioning agents also tend to be irritating, further detracting from the appeal of the overall product to the consumer.

The vehicle in which the functional components are applied is also a factor in the consumer's acceptance of a product. Styling products capable of providing a substantial amount of hold have traditionally been lotions or gels; however, many lotions can be runny and difficult to control when applied, and gels, although more controllable by the user, frequently provide a heavy, stiff feeling to the hair. Both types of products can also be sticky and unpleasant to the touch. Perhaps more favored today is a foaming mousse-type product, which is perceived as light, gentle, and easy to control on application to the hair. However, aerosol foams have fallen into great public disfavor, due to the potentially harmful effect of the propellants used. There are now available a variety of non-aerosol pumps which, in combination with the proper composition, can yield a foamy product without the use of environmentally harmful propellants. However, obtaining the foam in the product necessitates the use of one or more foaming agents, which can not only interfere with the holding properties of the styling polymer, but also can cause considerable irritation.

It is clear, then, that a need continues to be felt for a multipurpose hair styling product which effectively combines control, conditioning and ease of application in a single composition, substantially without any irritation. The present invention now provides a product with such a unique combination of properties.

SUMMARY OF THE INVENTION

The invention relates to an aqueous foaming hair care composition comprising effective amounts of a foaming agent, a water soluble quaternized vinylpyrrolidone/acrylate or methacrylate copolymer, and a water soluble quaternized cellulose derivative. The compositions so prepared provide a non-irritating formulation which balances the competing needs of hair styling and control, with an excellent measure of conditioning, and yield a rich mousse-like foam when dispensed from a non-aerosol container.

DETAILED DESCRIPTION OF THE INVENTION

The compositions of the invention comprise a unique combination of styling, conditioning and foaming agents, which provide a variety of benefits to the hair. A first component is a conditioning component, which is a quaternary derivative of a cellulose ether. Such compounds are wellknown, and are described, for example, in French Patent No. 1,492,597, and U.S. Pat. No. 3,472,840, the contents of which are incorporated herein by reference. Generally speaking, the derivatives are of the formula:

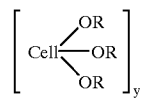

wherein Cell is the residue of an anhydroglucose unit, y is a whole number between about 50 and about 20,000, and preferably between 200 and 5000, and the radicals R, either the same or different, are a group of the formula:

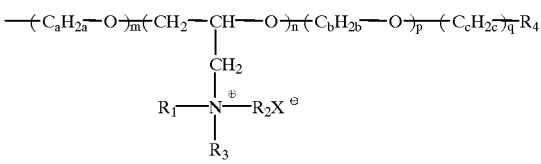

wherein a and b are 2 or 3; c is 1,2, or 3; m and p are whole numbers from 0 to 10; n is a whole number from 0–3; q is 0 or 1; $R_1$, $R_2$, and $R_3$ are each independently alkyl, aryl, aralkyl, alkaryl, cycloalkyl, alkoxyalkyl or alkoxyaryl, containing 1–10 carbon atoms and such that the sum of the number of carbon atoms of $R_1$, $R_2$, and $R_3$ varies from 3 to 12, provided that when any one of $R_1$, $R_2$, and $R_3$ is alkoxyalkyl, there are at least two carbon atoms between the oxygen of the alkoxy moiety and the nitrogen atom to which the alkyl moiety is attached; and X represents the anionic residue of a mineral or organic acid. $R_4$ is selected from H,

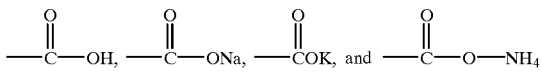

with the proviso that when q is 0, then $R_4$ is H.

Representative anions designated as XO, include chloride, bromide, sulfate, bisulfate, $CH_3SO_3^-$, sulfonate, phosphate, acetate and the like.

The average value of n is between about 0.01 and 1 per anhydroglucose unit, and preferably between about 0.1 and 0.5. The average value of (m+n+p+q) is between about 0.01–4 per unit of anhydroglucose.

The compounds are prepared by the etherification of a cellulose chain with a short chain alkyl or hydroxyalkyl, in the presence of an alkylating agent, followed by quaternization with a quaternary halohydrin. In a preferred embodiment, the compounds are prepared starting with a cellulose ether selected from the group consisting of non-ionic water-soluble cellulose ethers and alkyl- or-hydroxyalkyl-substituted non-ionic water soluble cellulose ethers. More preferably, the derivatives are methyl-, ethyl- or hydroxyethyl cellulose. In a particularly preferred embodiment, the cationic polymer is polyquaternium-10, a polymeric quaternary ammonium salt of hydroxyethyl cellulose reacted with a trimethyl ammonium substituted epoxide. Such polymers are commercially available from Amerchol under the tradename UCARE Polymer JR.

A second component is styling polymer which provides hold and body to the hair. This component is a film forming acrylate or methacrylate polymer or copolymer compatible with use on the hair. A large number of different polymers of this type are available commercially. Examples of such can be found in the International Cosmetic Ingredient Handbook, Third Edition, CTFA, 1995, the contents of which are incorporated herein by reference; these include, but are not limited to, acrylates copolymer and octylacrylamide/acrylates/butylaminoethyl methacrylate copolymer. In a preferred embodiment, the styling agent is a quaternized N-vinylpyrrolidone/acrylate or methacrylate copolymer. In particular, the styling copolymers have the formula:

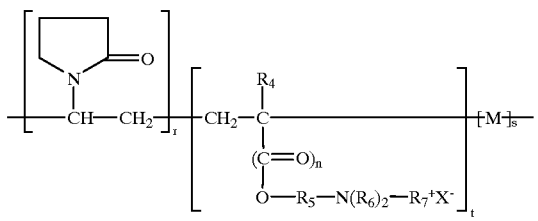

wherein, on the basis of 100 moles of monomer units, r is a whole number between 20 and 99, s is a whole number between 1 and 80, s is whole number between 1 and 80, and t is whole number between 0 and 50; n=0 or 1; $R_4$ is hydrogen or methyl; $R_5$ is

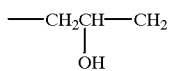

or $C_xH_{2x}$, wherein x is a whole number between 2 and 18; $R_6$ is methyl, ethyl or tert-butyl; $R_7$ is methyl, ethyl or benzyl; $X^-$ is a chloride, bromide, iodide sulfate, bisulfate, or $CH_3SO_3^-$ anion; and M represents a copolymerizable vinyl monomer unit. The optionally present M in the formula is a conventional vinyl monomer copolymerizable with N-vinyl pyrrolidone, including, but not limited to, alkyl vinyl ethers, alkyl esters of acrylic or methacrylic acid, vinyl aromatic monomers, vinyl esters, acrylonitrile, vinyl chloride, methacrylamide, alkyl crotonates, and the like.

The preferred acrylates or methacrylates are the acrylate or methacrylate of di-lower alkyl-amino alkyl or the acrylate or methacrylate of di-lower alkyl amino hydroxyalkyl. Examples of such acrylates or methacrylates include: dimethylamino methyl acrylate, dimethylaminomethyl methacrylate, diethylaminomethyl acrylate, diethylaminomethyl methacrylate, dimethylaminoethyl acrylate, dimethylaminoethyl methacrylate, dimethylamino-2-hydroxypropyl acrylate, dimethylamino-2-hydroxypropyl methacrylate, diethylamino-2-hydroxyethyl acrylate, diethylamino-2-hydroxyethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate, and diethylaminooctyl acrylate. The molecular weight of these polymers can range from about 15,000 to over 1,000,000. A particularly preferred example of these polymers is polyquaternium-11, which is the quaternary ammonium polymer formed by the reaction of diethyl sulfate and a copolymer of vinyl pyrrolidone and dimethyl aminoethylmethacrylate, and is commercially available under the name GAFQUAT 755N, from ISP.

The effective amounts of each of these components can be varied, but generally the styling polymer will be in the range of from about 1–15%, preferably about 1–10%, by weight of the total composition, the higher end of the range being employed with lower viscosity, lower molecular weight polymers. The conditioning polymer will be used in an amount of from about 0.05–1%, preferably 0.05–0.5, by weight of the total composition. It is particularly preferred that there be a substantial excess of the styling polymer, so that the ratio of components is from about 5:1 to about 100:1, more preferably from about 10:1 to about 50:1. These ratios prevent the conditioning agent from interfering with the hold provided by the primary styling resin.

A third component of the formulation is a water-soluble foaming agent. In principle, any such agent can be employed; these agents are also well-known in the art, and examples can be found in the International Cosmetic Ingredient Dictionary, Volume 2, Sixth Edition, 1995, CTFA, the contents of which are incorporated herein by reference. Preferably, however, the foaming agent is one which is relatively non-irritating. Examples of such materials include, but are not limited to, polysorbates, polyglyceryl esters, betaines, taurates, and imidazoline amphoterics. Particularly preferred are polysorbates. Generally speaking, the amount of foaming agent should be kept fairly low, so as not to interfere with the styling and conditioning properties of the other polymers. As a guideline, the foaming agent is preferably present in an amount of from about 0.1–5%, preferably from about 0.5–3%, by weight of the total composition.

The remainder of the composition may simply be water, i.e., any cosmetically acceptable water based material, such as deionized water, or a floral or herbal water. More frequently, it is the case that additional hair care components are present. Examples of additional categories of components which may be added to the basic components of the formulation are emollients and additional conditioners, ethanol, fragrance, sunscreens, preservatives, and antioxidants. Appropriate examples of such materials can also be found in the International Cosmetic Ingredient Dictionary, supra.

Although the composition can be packaged in any type of pump package, the benefits of the compositions of the invention are best achieved when packaged in and dispensed from a manually operated, non-aerosol pump foam dispenser. Such dispensers are described, for example, in EP 621796 and WO 97/13585. Other examples are also commercially available. A particularly preferred apparatus of this type is available commercially from Airspray® under the name F2 Finger Pump Foamer.

The advantages of the compositions of the invention are many. When dispensed through a pump foaming apparatus, the compositions yield a light mousse-like foam that is easily applied to either wet or dry hair. The product provides volume and body to hair, along with light-weight control, conditioning, improved wet and dry combing, flyaway control, and detangling properties, without the stickiness, heaviness, or flaking commonly associated with more traditional styling products such as lotions or gels.

The invention is further illustrated by the following non-limiting example.

| Material | Weight % |
|---|---|
| Water | QS |
| Polyquaternium-10 | 0.100 |
| Polyquaternium-11 (20% solution) | 6.000 |
| Fragrance | 0.300 |
| Glycerin | 2.000 |
| Polysorbate 20 | 2.500 |
| Tocopherol | 0.001 |

The product is prepared as follows:

Polyquaternium-10 is added to water with moderate agitation. Sodium hydroxide is added until pH reaches 6–7, and then mixing is continued until the polymer is hydrated. Polyquaternium-11 is then added and mixed until dissolved. Glycerin is then added and mixed until dissolved. The fragrance, polysorbate-20 and tocopherol are premixed to homogeneity, and then added to the batch, mixing until dissolved. The pH is finally adjusted to 6.0–6.5.

What we claim is:

1. A cosmetic composition for topical application to the hair comprising about 0.1 to about 5% by weight of a foaming agent, about 1 to about 15% by weight of a water soluble film-forming quaternized vinylpyrrolidone/acrylate or methacrylate copolymer, and about 0.05 to about 1% by weight of a water soluble quaternized cellulose derivative.

2. The composition of claim 1 in which the cellulose derivative is a reaction product of a non-ionic water-soluble cellulose ether or an alkyl- or-hydroxyalkyl-substituted non-ionic water soluble cellulose ether with a trimethyl ammonium substituted epoxide.

3. The composition of claim 2 in which the cellulose ether is a hydroxyalkyl substituted cellulose ether.

4. The composition of claim 1 in which the cellulose derivative is polyquaternium-10.

5. The composition of claim 1 in which the copolymer is a copolymer of N-vinyl pyrrolidone and di-lower alkyl-amino alkyl acrylate, di-lower alkyl-amino alkyl methacrylate, di-lower alkyl-amino hydroxyalkyl acrylate, or di-lower alkyl-amino hydroxyalkyl methacrylate.

6. The composition of claim 1 in which the quaternized copolymer is polyquaternium-11.

7. The composition of claim 1 in which the foaming agent is a polysorbate.

8. The composition of claim 1 in which the foaming agent is polysorbate 20.

9. A cosmetic composition for topical application to the hair comprising about 0.1 to about 5% by weight of a polysorbate foaming agent, about 1 to about 15% by weight of a water soluble quaternized copolymer of N-vinyl pyrrolidone and di-lower alkyl-amino alkyl acrylate, di-lower alkyl-amino alkyl methacrylate, di-lower alkyl-amino hydroxyalkyl acrylate, or di-lower alkyl-amino hydroxyalkyl methacrylate, and about 0.05 to about 1% by weight of a water soluble quaternized cellulose derivative which is a reaction product of a non-ionic water-soluble cellulose ether or an alkyl- or-hydroxyalkyl-substituted non-ionic water soluble cellulose ether with a trimethyl ammonium substituted epoxide.

10. The composition of claim 9 which comprises a polysorbate foaming agent, a quaternized copolymer of di-lower-alkyl-amino alkyl acrylate or di-lower alkyl-amino alkyl methacrylate, and a quaternized hydroxyalkyl substituted cellulose ether.

11. The composition of claim 9 which comprises polysorbate 20, polyquaternium-11, and polyquaternium-10.

12. The composition of claim 9 in which the foaming agent is present in an amount of from about 0.1–5%, the quaternized copolymer is present in an amount of from about 1–15%, and the cellulose derivative is present in an amount of from about 0.05–1%, all by weight of the total composition.

13. The composition of claim 9 in which the foaming agent is present in an amount of from about 0.5–3%, the quaternized copolymer is present in an amount of from about 1–10%, and the cellulose derivative is present in an amount of from about 0.05–0.5%, all by weight of the total composition.

14. The composition of claim 11 in which the foaming agent is present in an amount of from about 0.5–3%, the quaternized copolymer is present in an amount of from about 1–10%, and the cellulose derivative is present in an amount of from about 0.05–0.5%, all by weight of the total composition.

15. The composition-of claim 9 in which the quaternized copolymer and the cellulose derivative are present in a ratio of from about 5:1 to about 100:1.

16. The composition of claim 15 in which the ratio is from about 10:1 to about 50:1.

17. A non-aerosol pump foaming apparatus comprising the composition of claim 1.

18. A non-aerosol pump foaming apparatus comprising the composition of claim 9.

19. A non-aerosol pump foaming apparatus comprising the composition of claim 10.

20. A non-aerosol pump foaming apparatus comprising the composition of claim 14.

* * * * *